United States Patent [19]

Bouchard

[11] Patent Number: 4,694,846

[45] Date of Patent: Sep. 22, 1987

[54] GARBAGE TRUCK WITH TRASH BIN CLEANING SYSTEM

[76] Inventor: Roland D. Bouchard, 15419 Doty Ave., Lawndale, Calif. 90260

[21] Appl. No.: 905,197

[22] Filed: Sep. 9, 1986

[51] Int. Cl.[4] .......................... B08B 3/02; B08B 9/08; A61L 11/00

[52] U.S. Cl. ................................ 134/78; 134/115 R; 134/152; 134/153; 134/170; 134/171; 422/302; 422/303

[58] Field of Search ...................... 134/52, 53, 62, 78, 134/95, 99, 104, 115 R, 152, 153, 166 R, 170, 171, 199; 422/302, 303

[56] References Cited

U.S. PATENT DOCUMENTS

| | | | |
|---|---|---|---|
| 3,207,166 | 9/1965 | Wintzer | 134/152 X |
| 3,212,511 | 10/1965 | Cuillier | 134/152 X |
| 3,291,144 | 12/1966 | Diamond | 134/170 X |
| 3,324,866 | 6/1967 | Davis | 134/115 R X |
| 3,372,875 | 3/1968 | Torrey | 134/115 R X |
| 3,881,950 | 5/1975 | Pettit | 134/115 R |
| 3,901,255 | 8/1975 | Pettit | 134/171 X |
| 4,211,745 | 7/1980 | Boyd | 134/115 R X |
| 4,242,311 | 12/1980 | Middaugh | 422/302 |

FOREIGN PATENT DOCUMENTS

| | | | |
|---|---|---|---|
| 1239903 | 7/1971 | United Kingdom | 134/115 R |

*Primary Examiner*—Philip R. Coe
*Attorney, Agent, or Firm*—Edward A. Sokolski

[57] ABSTRACT

A garbage truck for handling large trash bins has a system incorporated therein for cleaning and deodorizing the bins after they have been emptied. Immediately after a bin has been emptied into the garbage truck trash compactor and while it is in an inverted position, the bin is sprayed with hot water ejected from nozzles mounted on the truck to the rear of the compactor. This spraying operation is controlled from the cab of the truck and is continued long enough with a large enough volume of water to insure thorough cleaning of the bin. After the bin has been washed it is returned to its original position on the ground and sprayed with deodorant from jet nozzles mounted on the top of the truck cab, this operation also being controlled by an operator in the cab.

6 Claims, 4 Drawing Figures

GARBAGE TRUCK WITH TRASH BIN CLEANING SYSTEM

This invention relates to garbage trucks and more particularly to a garbage truck having a system for cleaning and deodorizing trash bins incorporated therein.

The disposal of trash and garbage from commercial establishments and apartment houses is generally handled by garbage trucks equipped to handle large trash bins which are generally employed. These trucks having the capability of lifting the bins and dumping the contents thereof into a compactor from where the compacted trash is pushed by a ram into the back of the truck for dumping. Particularly in the case of restaurants and apartment houses where the trash contains a considerable amount of organic material, the bins which are left standing after having been emptied become unpleasantly odorous and can present a health problem.

The system of the present invention obviates this problem by providing a system for washing and deodorizing the bins after they have been dumped. This end result is achieved rapidly and efficiently by thoroughly spraying the bins with hot water immediately after they have been emptied and subsequently when the bins have been returned to their original standing position by spraying such bins with a deodorant.

It is therefore an object of this invention to provide means for cleaning and deodorizing trash bins immediately after they have been emptied into a garbage truck.

It is another object of this invention to provide a semiautomatic system for rapidly and efficiently cleaning and deodorizing trash bins when they are emptied into a garbage truck.

Other objects of this invention will become apparent as the description proceeds in connection with the accompanying drawings of which:

Figure 1:
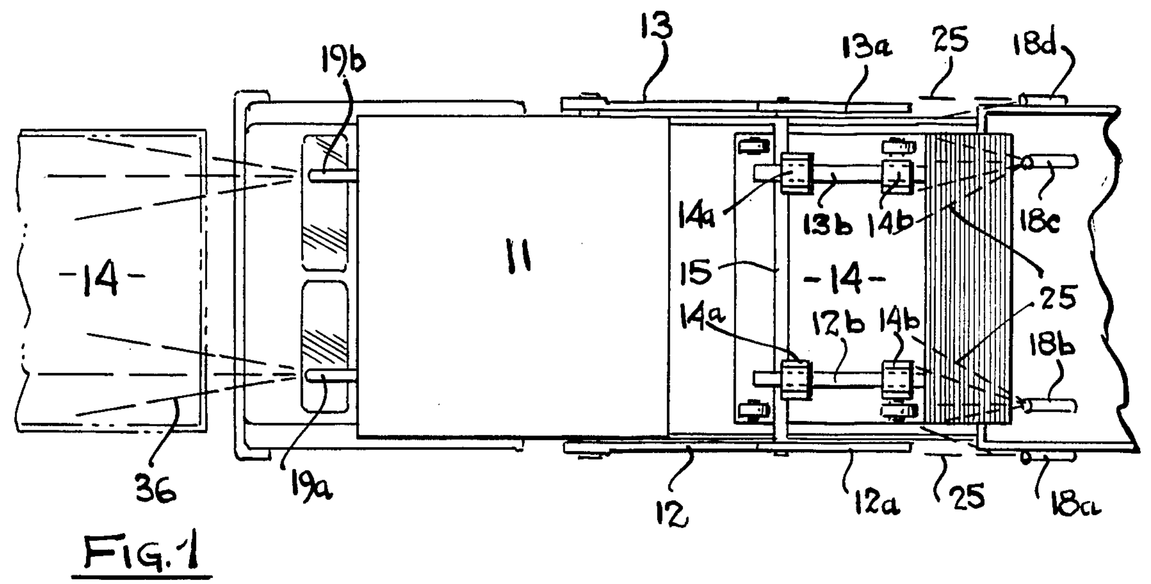
FIG. 1 is a top plan view illustrating a preferred embodiment of the system of the invention.
Figure 2:
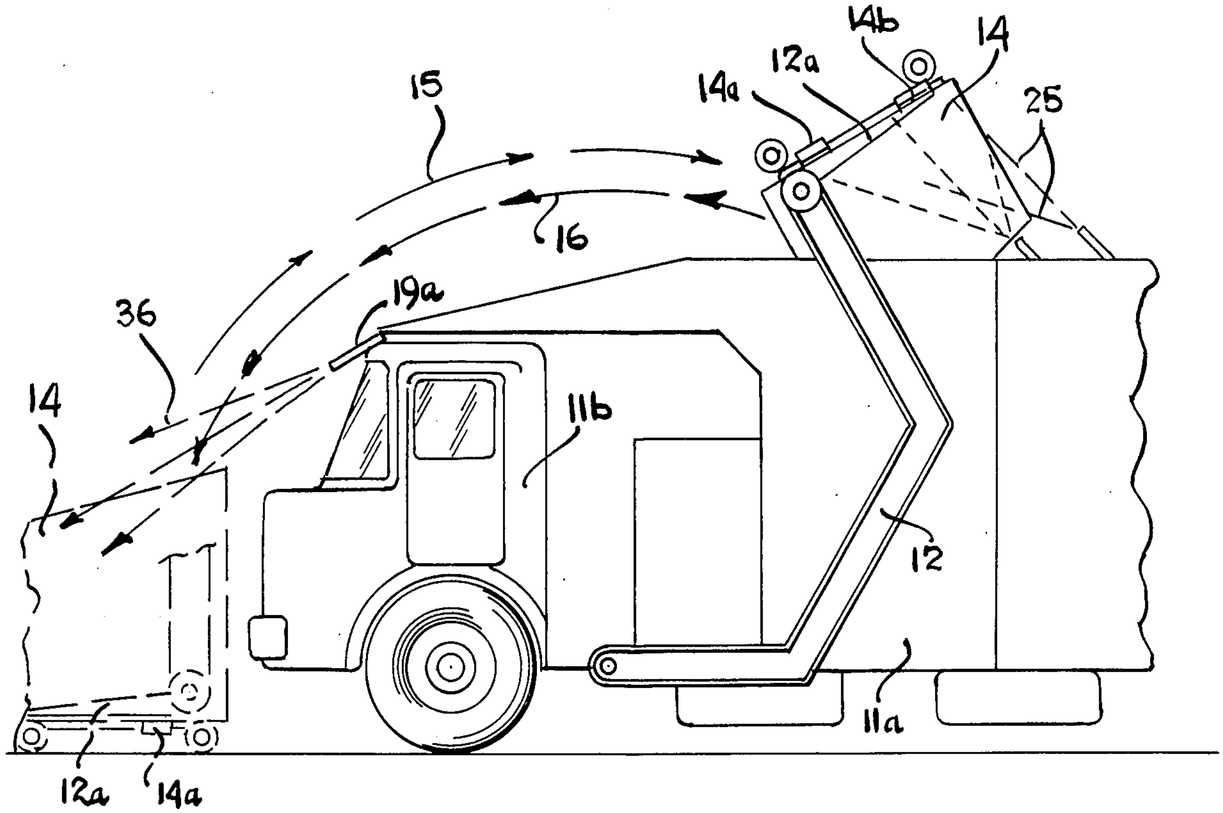
FIG. 2 is a side elevational view of the embodiment of FIG. 1.

Referring now to FIGS. 1 and 2 a preferred embodiment of the system of the invention is shown.

Garbage truck 11 has a pair of opposing conveyor arms 12 and 13 which are driven by suitable motor drive (not shown) between the elevated position show in the figures and a lowered position shown in FIG. 2 in phantom, as indicated by arrows 15 and 16 respectively. This structure is conventional and forms no part of the present invention. The arms 12 and 13 have outer forks 12*a* and 13*a* and inner forks 12*b* and 13*b* which extend from cross bar 15 which interconnects their extremities. The inner forks 12*b* and 13*b* fit through "U" brackets 14*a* and 14*b* formed on the bottom of trash bin 14.

A first set of four jet spray nozzles 18*a*–18*d* is mounted on the top of the truck immediately to the rear of the trash compacting bin 11*a* of the truck. A second set of jet spray nozzles 19*a* and 19*b* is mounted on the top of the cab 11*b* of the truck.

Figure 3A:
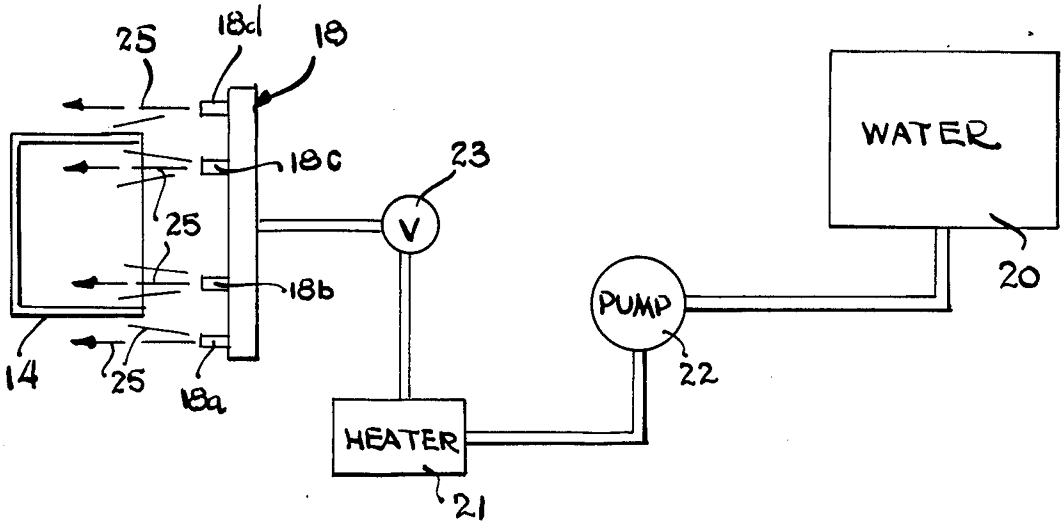
FIG. 3A is a schematic drawing illustrating the water spraying operation of the system of the invention.

Referring now to FIG. 3A water is fed from tank 20 to heater 21 where it is heated to a temperature of approximately 200° F. The water is pumped by means of pump 22 at a pressure of about 3,000 psi through valve 23 to nozzle assembly 18. Streams of water 25 are emitted from nozzles 18*a*–18*d* to thoroughly spray the interior and exterior walls of trash bin 14, a first pair of such nozzles 18*a* and 18*d* spraying the outer walls a second pair 18*b* and 18*c* spraying the inner walls.

Figure 3B:
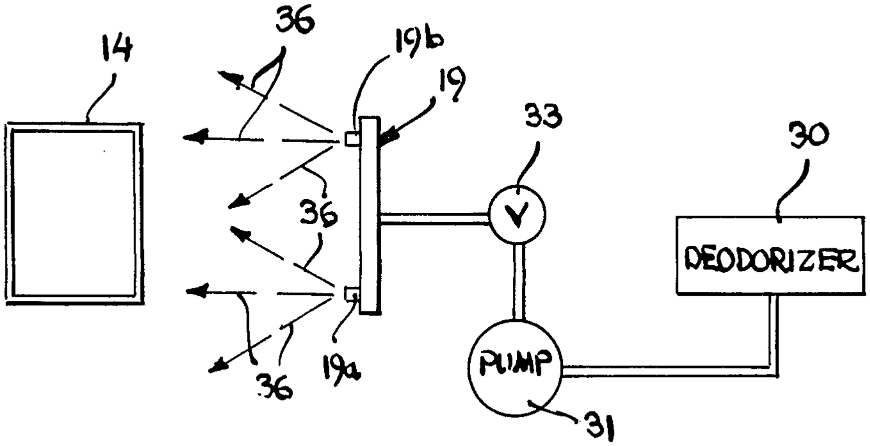
FIG. 3B is a schematic drawing illustrating the deodorizing operation of the system of the invention.

Referring now to FIG. 3B, the deodorizing sub-system is schematically illustrated. The deodorizer contained in tank 30 is pumped by means of pump 31 through valve 33 to nozzle assembly 19. The deodorizer is typically pumped at a pressure of 3 psi at the rate of 2 gallons/minute. Sprays 36 of deodorizer are emitted from jet nozzles 19*a*–19*b* to spray both the inner and outer walls of trash bin 14.

In operation, with conveyor arms 12 and 13 in the lowered position, as indicated by the dotted outline in FIG. 2, the truck is first driven to bring forks 12*a* at the ends of each of the arms into brackets 14*a* and 14*b* on the bottom of bin 14. The arms are then elevated as indicated by arrows 15 to bring the bin to an inverted position above trash compactor compartment 11*a* as shown in FIGS. 1 and 2. After the trash has been emptied from the bin into the trash compactor compartment 11*a* and the compacted trash pushed out of the compactor by means of a suitable ram, the water spraying nozzles 18*a*–18*d* are activated and such spraying continued by means of manual control of valve 23 from within the cab 11*b*. When the spraying operation has been completed the trash bin 14 is lowered by means of conveyor arms 12 and 13 back to the position shown in dotted outline, as indicated by arrows 16. With the bin 14 on the ground, as shown in dotted outline, valve 33 is manually controlled to emit deodorant from jet valves 19*a* and 19*b* so as to thoroughly spray the bin.

Thus, the system of the invention provides a semiautomatic means for both washing and deodorizing a trash bin immediately after its contents has been dumped into a garbage truck and after the bin has been returned to its initial position on the ground, respectively.

While the invention has been described and illustrated in detail, it is to be clearly understood that this is intended by way of illustration and example only and is not to be taken by way of limitation, the spirit and scope of this invention being limited only by the terms of the following claims.

I claim:

1. In a garbage truck for removing garbage contained in a trash bin, said truck including a compartment for receiving garbage from said bin, a cab for the operator of the truck and conveyor arm means for lifting the bin from a first upright position on the ground to a second inverted position above said compartment whereat the garbage is emptied into the compartment and then returned back to its initial upright position on the ground, the improvement being means for washing and deodorizing said trash bin comprising:

a first set of spray nozzles mounted on said truck behind the compartment, means for feeding a washing liquid to said first set of nozzles when the bin is on its inverted position and after the bin has been emptied, said first set of nozzles being positioned to direct sprays of said washing liquid against the interior and exterior walls of said bin, a second set of spray nozzles mounted on the cab of the truck, and means for feeding deodorizing liquid to said second set of nozzles after the bin has been sprayed from first set of nozzles and has been returned to its upright position on the ground, said second set of nozzles being positioned to direct sprays of said deodorizing liquid against the interior and exterior walls of said bin.

2. The combination of claim 1 wherein said first set of nozzles includes a pair of outer nozzles for directing sprays against the outer walls of the bin and a pair of inner nozzles for directing sprays against the inner walls of the bin.

3. The combination of claim 1 wherein the second set of nozzles includes a pair of nozzles for directing sprays against both the inner and outer walls of the bins.

4. The combination of claim 1 wherein the washing liquid is hot water.

5. The combination of claim 4 wherein the means for feeding the washing liquid to the first set of nozzles comprises first pump means for pressurizing the liquid and a first control valve receiving said liquid from said first pump means, the washing liquid being fed from the first valve to the first set of nozzles.

6. The combination of claim 5 wherein the means for feeding the deodorizing liquid to the second set of nozzles comprises second pump means for pressurizing the deodorizing liquid and a second control valve receiving the deodorizing liquid from said second pump means, the deodorizing liquid being fed from the second valve to the second set of nozzles.

* * * * *